(12) United States Patent
Bhat et al.

(10) Patent No.: US 8,870,815 B2
(45) Date of Patent: Oct. 28, 2014

(54) STEERING SYSTEM AND A CATCHER SYSTEM

(75) Inventors: Ravindra Bhat, Eindhoven (NL);
Dennis Erwin Bos, Eindhoven (NL);
Antonius Maria Rijken, Eindhoven (NL); Michel Gerardus Pardoel, Eindhoven (NL); Sait Izmit, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 132 days.

(21) Appl. No.: 13/508,560

(22) PCT Filed: Nov. 8, 2010

(86) PCT No.: PCT/IB2010/055056
§ 371 (c)(1),
(2), (4) Date: May 8, 2012

(87) PCT Pub. No.: WO2011/058493
PCT Pub. Date: May 19, 2011

(65) Prior Publication Data
US 2012/0232476 A1  Sep. 13, 2012

(30) Foreign Application Priority Data

Nov. 12, 2009 (EP) ................................ 09175746

(51) Int. Cl.
*A61M 31/00* (2006.01)
*A61B 19/00* (2006.01)
*A61B 1/00* (2006.01)
*A61M 25/09* (2006.01)
*A61M 25/01* (2006.01)
*A61B 8/00* (2006.01)
*A61B 8/12* (2006.01)

(52) U.S. Cl.
CPC ........ *A61M 25/0113* (2013.01); *A61B 19/2203* (2013.01); *A61B 1/00147* (2013.01); *A61B 2019/2211* (2013.01); *A61M 25/09041* (2013.01); *A61B 8/42* (2013.01); *A61B 8/12* (2013.01)
USPC ....................................................... 604/95.01

(58) Field of Classification Search
USPC ........................ 604/95.01, 156; 226/176, 182
See application file for complete search history.

(56) References Cited

U.S. PATENT DOCUMENTS 3,317,779 A * 5/1967 Henderson ........................ 314/5
6,398,755 B1 6/2002 Belef et al.

(Continued)

FOREIGN PATENT DOCUMENTS

| DE | 102004007935 | 5/2005 |
| WO | WO2005084122 | 9/2005 |
| WO | WO2009092059 | 7/2009 |

*Primary Examiner* — Nicholas Lucchesi
*Assistant Examiner* — Weng Lee

(57) ABSTRACT

A steering system (30) comprises two radially oppositely arranged drive wheels (1; 3) for steering a tubular object (5) positioned between the drive wheels (1; 3). The drive wheels (1; 3) each have a wheel rotation axis (40; 42) and each include a plurality of rollers (7) distributed around the wheel rotation axis (40; 42). The rollers (7) are rotatably arranged, each roller having a roller rotation axis (44) and an outer drive face (58) concavely vaulted in a direction corresponding to its roller rotation axis (44). The roller rotation axis (44) is obliquely oriented in relation to the wheel rotation axis (40; 42) and the rollers (7) of each drive wheel (1; 3) form together a steering periphery for the tubular object (5). The steering system enables continues rotation of a tubular object without danger that the object will lose the contact with the rollers. The steering system (30) may be incorporated in a catheter system which comprises a catheter (5).

13 Claims, 4 Drawing Sheets

(56) References Cited

U.S. PATENT DOCUMENTS 6,726,675 B1 4/2004 Beyar
2004/0254566 A1* 12/2004 Plicchi et al. .................... 606/1
2008/0009791 A1 1/2008 Cohen et al.

* cited by examiner

STEERING SYSTEM AND A CATCHER SYSTEM

FIELD OF THE INVENTION

The invention relates to a steering system comprising two radially oppositely arranged drive wheels for steering a tubular object positioned between the drive wheels.

The invention also relates to a catheter system comprising such a steering system.

BACKGROUND OF THE INVENTION

An embodiment of such a steering system, viz. a catheter system, is disclosed in patent application US 2004/0254566 A1. The known system includes an apparatus comprising two rollers arranged parallel to each other and orthogonally to a catheter, which is gripped between these rollers. At least one of the rollers can be rotatably driven, and at least one of the said rollers is pressed elastically against the other to provide a frictional clamping of the interposed catheter. As a result of a roller's rotation in the clockwise or anti-clockwise direction the catheter moves longitudinally forwards or backwards respectively. Also, at least one of the two rollers can be axially moved in both of its axial directions in such a way that as a result of this axial movement the catheter gripped between the rollers is rotated rightwards or leftwards respectively about its own axis. The use of a single pair of rollers that are engaged with the catheter produces both the longitudinal forward and backward movements of the catheter, and its rightward or leftward rotation possibly simultaneously with the said longitudinal movement.

In the known apparatus rotations of the catheter are linked to movements of the catheter along the rollers' axial axes. A drawback thereof is that the number of rotations of the catheter is limited by the axial size of the rollers. In particular, if the catheter is continuously rotated the catheter will lose the contact with the rollers at certain moment as a consequence of its replacement along the rollers' axes and will not be gripped by rollers. Once this happens the movement of the catheter cannot be controlled by rollers any more.

SUMMARY OF THE INVENTION

It is an object of the present invention to provide a better steering system that enables continues rotation of a tubular object without danger that the tubular object will lose the contact with the rollers.

This object is achieved with the steering system according to the invention as defined in Claim 1. The steering system comprises two radially oppositely arranged drive wheels for steering a tubular object, for example a catheter, positioned between the drive wheels. It is noted that that the term "steering a tubular object" includes orientating and\or propagating the tubular object. The drive wheels each have a wheel rotation axis and each include a plurality of rollers distributed around the wheel rotation axis. The rollers are rotatably arranged. Each roller has a roller rotation axis and an outer drive face concavely vaulted in a direction corresponding to its roller rotation axis. The roller rotation axis is obliquely oriented in relation to the wheel rotation axis. The rollers of each drive wheel form together a steering periphery for the tubular object. In such a steering system the rotation of the tubular object does not produce the movement of the tubular object along the roller rotation axis. Such construction of the drive wheels and the rollers provides that the tubular object stays gripped by the rollers of the wheels regardless the amount of the rotation due to the roller's outer drive face which is concavely vaulted in a direction corresponding to its roller rotation axis. In conclusion, the steering system according to the invention does not possesses the above described problem of the above mentioned prior art apparatus.

An embodiment of the steering system according to the invention has the feature that the the steering system comprises a motor device for driving the drive wheels.

Steering the tubular object using the steering system according to the invention works as described hereinafter. The tubular object is moved in a first axial direction when the motor steers one of the drive wheels, further mentioned first wheel, counter clockwise and the other drive wheel, further mentioned second wheel, clockwise. The tubular object is moved in a second axial direction when the motor steers the first wheel clockwise and the second wheel counter clockwise. The tubular object is rotated in the first rotational direction when the motor steers the first wheel clockwise and the second wheel clockwise. The tubular object is rotated in the second rotational direction, opposite of the first rotational direction, when the motor steers the first wheel counter clockwise and the second wheel counter clockwise.

A practical embodiment of the steering system according to the invention has the feature that the each drive wheel includes two wheel flanges extending around the rotation axis. The rollers are mounted between the two wheel flanges.

A practical embodiment of the steering system according to the invention has the feature that the wheel rotation axes are substantially parallelly arranged with respect to each other.

A practical embodiment of the steering system according to the invention has the feature that the roller rotation axis forms an angle between 10 and 80 degrees with the wheel rotation axis. The angle of preferably between 30 and 60 degrees enables a good gripping of the tubular object by the rollers.

A preferred embodiment of the steering system according to the invention has the feature that the roller rotation axis forms an angle of substantially 45 degrees with the wheel rotation axis. Such angle provides a best grip of the tubular object by the rollers.

An embodiment of the steering system according to the invention has the feature that the drive wheels are moveable between a first position in which the driving wheels are close to each other for driving the tubular object and a second position in which the driving wheels are remote to each other for plugging in and\or out the tubular object.

Such a feature provides a possibility to a user of the steering system to detach the tubular object from the system and to continue to steer the tubular object manually.

An embodiment of the steering system according to the invention has the feature that the steering system comprises a drive wheels control device for moving the drive wheels between the first position and the second position.

The steering system according to the invention can be used in a variety of applications, such as catheter or guide wire steering, non-invasive surgical or investigative tool steering and ultrasonic probe steering in a human or an animal body.

It is also an object of the present invention to provide a catheter system. The catheter system according to the invention comprises a catheter and the steering system according to the invention. The catheter constitutes the tubular object and the steering system is configured to steer the catheter.

An embodiment of the catheter system according to the invention has the feature that the catheter comprises a tip and that the catheter system comprises a drive unit for manipulating the tip. The drive unit may be any drive unit known in the art and can be used by a user of the catheter system in order to execute a desired operation on a body, particularly a human or animal body, once the tip is driven to the required position within the body.

An embodiment of the catheter system according to the invention has the feature that the catheter system comprises a motor steering device for steering the motor device of the steering system.

The motor steering device may be a microprocessor unit known in the art provided with suitable software for steering the steering system. The microprocessor unit can be controlled by the user via a control table with command buttons. By pressing an appropriate button the user can choose to translate the tubular object in one of two axial directions and/or to rotate the tubular object in one of two rotational directions. Accordingly, during use, the motor device receives a steering command from the microprocessor and steers the wheels of the steering system in the way that the chosen translation and/or rotation of the tubular object is achieved.

An embodiment of the catheter system according to the invention has the feature that the catheter system comprises a tracking means for determining a position and\or an orientation of the tip in a body and a display for displaying the position and\or the orientation of the tip determined by the tracking means.

During operation a user of the catheter system observes the position and\or the orientation of the tip and manipulates the tip of the catheter by the drive unit according to a required operation.

An embodiment of the catheter system according to the invention has the feature that the wheels of the steering system are constituted as a disposable unit, while the drive motors form a reusable assembly. Such implementation aids clean ability.

BRIEF DESCRIPTION OF THE DRAWINGS

In the following, the invention and further aspects will be described, by way of example, and explained hereinafter, using the following figures.

DETAILED DESCRIPTION OF THE EMBODIMENTS

In the following description of the preferred embodiments, reference is made to the accompanying drawings which form a part thereof. Specific embodiments, in which the invention may be practiced, are shown in the following description by a way of illustration. It is also understood that other embodiments may be utilized and structural changes may be made without departing from the scope of the present invention. It is noted that the same reference signs will be used for indicating the same or similar parts in the several embodiments.

Figure 1:
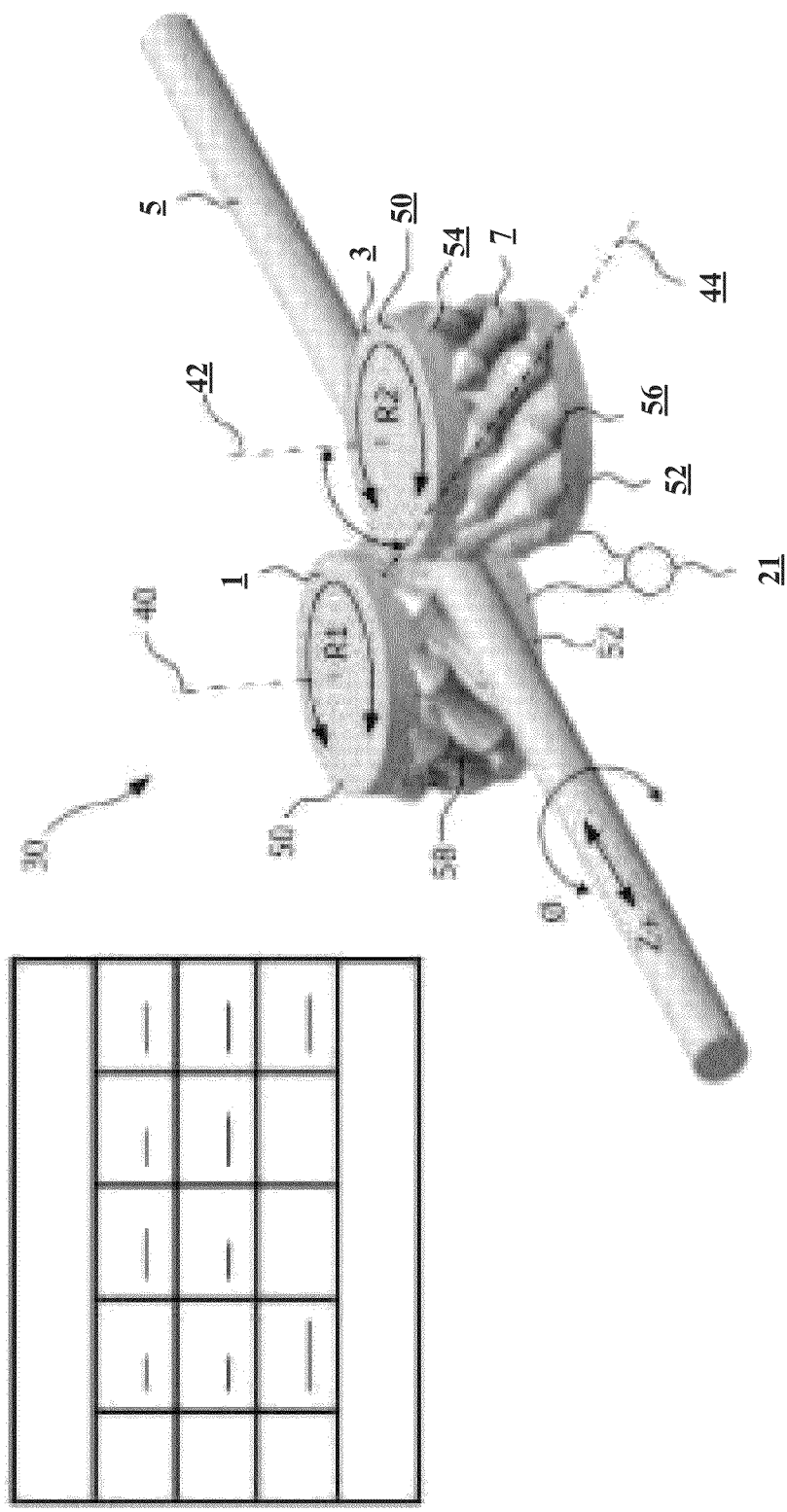
FIG. 1 schematically shows an exemplary embodiment of the steering system according to the invention.

A first embodiment of the invention, shown in FIG. 1 is depicted in a perspective view. A steering system 30 comprises two radially oppositely arranged drive wheels 1; 3 for steering a tubular object 5 positioned between the drive wheels 1; 3. The drive wheels 1; 3 each have a wheel rotation axis 40; 42 and each include a plurality of rollers 7 distributed around the wheel rotation axis 40; 42. In this embodiment each wheel 1 has 12 rollers. The rollers 7 are rotatably arranged and each roller has a roller rotation axis 44 and an outer drive face 58. The outer drive face is concavely vaulted in a direction corresponding to its roller rotation axis 44. The roller rotation axis 44 is obliquely oriented in relation to the wheel rotation axis 40; 42. The rollers 7 of each drive wheel 1; 3 form together a steering periphery for the tubular object 5. Each drive wheel 1; 3 includes two wheel flanges 50; 52 extending around and perpendicular to the rotation axis 40; 42. The rollers 7 are mounted between and bearded by the two wheel flanges 50; 52.

The system further comprises an electric motor device 21 for driving the drive wheels 1; 3. The system can also comprise two electric motors 21, wherein each of these two motors steers one of two wheels 1; 3.

The steering of the tubular object 5 using the steering system 30 according to the invention works as the following. The steering of the tubular object 5 is a consequence of friction between the tubular object 5 and the rollers 7 of both wheels 1; 3. The axial movement, Z− or Z+, of the tubular object 5 is achieved by steering the wheels 1; 3 in different directions in respect to each other. Concretely, the tubular object 5 is moved in a first axial direction Z− when the motor 21 steers the first wheel 1 counter clockwise ccw and the second wheel 3 clockwise cw, and the tubular object 5 is moved in a second axial direction Z+ when the motor 21 steers the first wheel 1 clockwise cw and the second wheel 3 counter clockwise ccw. The rotation, counter clock wise θccw or clockwise θcw, of the tubular object 5 is achieved by steering the wheels 1; 3 in the same direction in respect to each other. Concretely, the tubular object 5 is rotated in the first rotational direction, counter clock wise θccw, when the motor 21 steers the first wheel 1 clockwise cw and the second wheel 3 clockwise cw and the tubular object 5 is rotated in the second rotational direction, clock wise θcw, opposite from the first rotational direction θccw, when the motor 21 steers the first wheel 1 counter clockwise ccw and the second wheel 3 counter clockwise ccw.

The intensity of gripping the tubular object 5 by the rollers 7 is dependent on an angle that roller rotation axis forms with the wheel rotation axis. The steering system is fitted to work with any angle between 10 and 80 degrees. The angle preferably between 30 and 60 degrees enables a very good gripping of the tubular object 5 by the rollers 7. The angle of substantially 45 degrees provides the best gripping of the tubular object 5 by the rollers 7 and consequently the best steering results.

Figure 2:
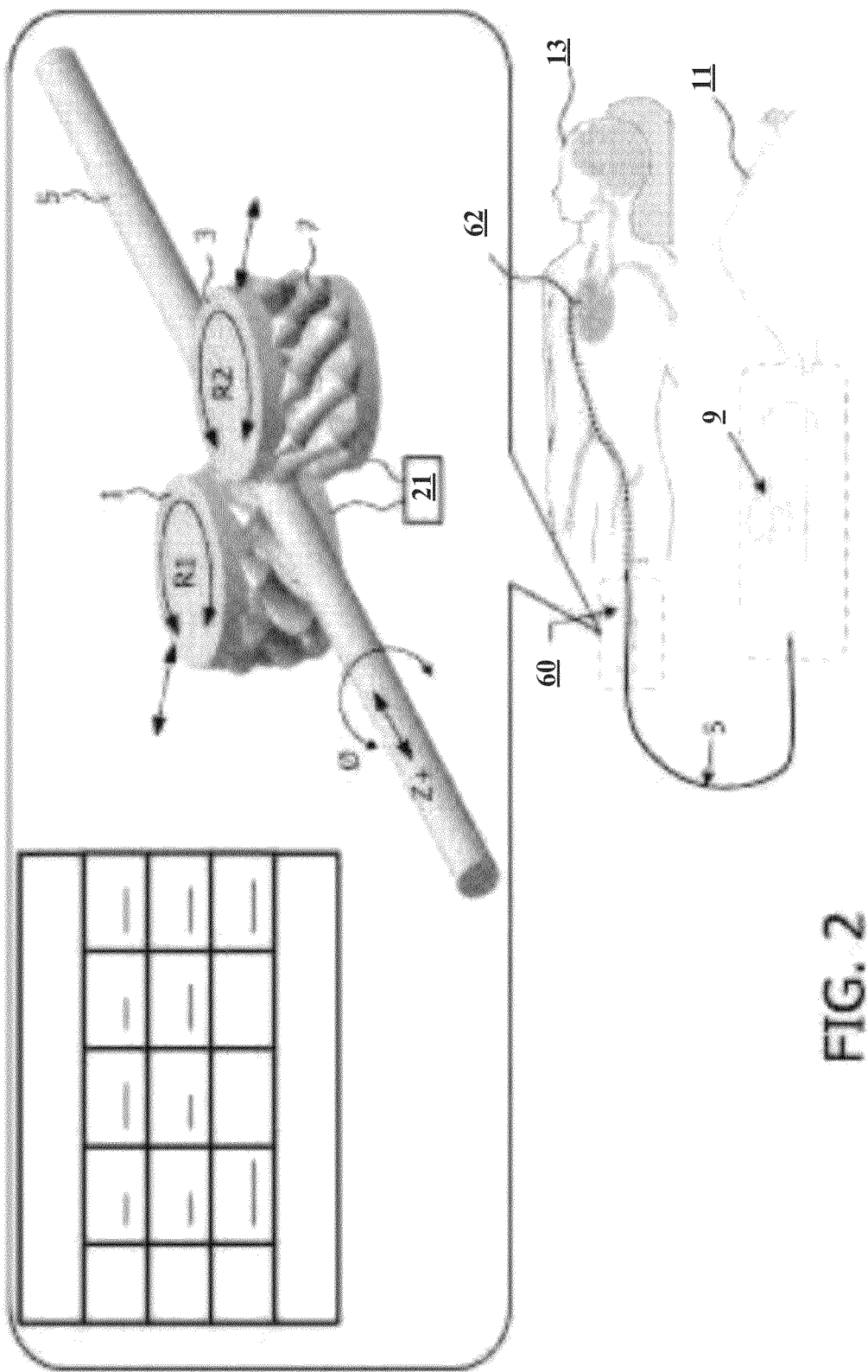
FIG. 2 schematically shows a first exemplary embodiment of the catheter system according to the invention and the position of the steering system within the catheter system.
Figure 3:
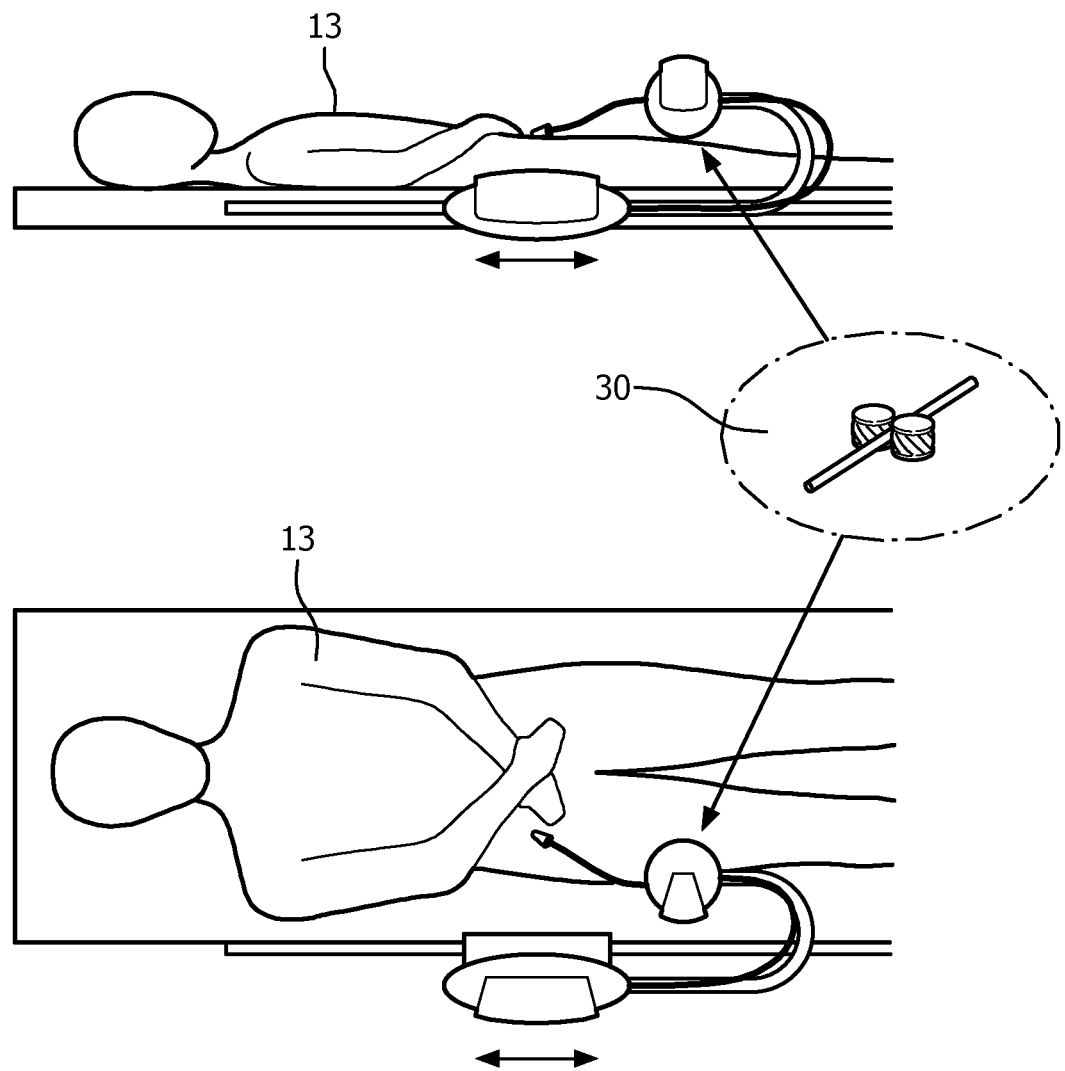
FIG. 3 schematically shows the first exemplary embodiment of the catheter system according to the invention, the position of the steering system within the catheter system and a possible position of the steering system in respect to a patient.

FIGS. 2 and 3 schematically show an exemplary embodiment of the catheter system according to the invention. A steering system 30 within the catheter system is positioned near by a body 13 of a human patient or an animal. A catheter 5 constitutes the tubular object. The steering system 30 has the feature that the drive wheels 1; 3 are moveable between a first position in which the driving wheels are close to each other for driving the catheter 5 and a second position in which the driving wheels are remote from each other for plugging in and\or out the catheter 5. Such feature provides a possibility to a user of the steering system to detach the catheter 5 from the steering system 30 and to continue to steer the tubular object manually. Such implementation may be required as a safety precaution. The steering system according to the invention has the feature that the steering system comprises a drive wheels control device 60 for moving the drive wheels 1; 3 between the first position and the second position. The drive wheels control device can be a motor or any other suitable device known in the art.

A possible implementation can be that the wheels having the rollers 7, which are during operation in contact with the catheter 5 and therefore with the patient's body 13, form a disposable unit, while the drive motors 21 form a reusable assembly to aid clean ability. That means that for each new patient a new catheter 5 and new wheels 1; 3 are used.

The catheter 5 comprises a tip 62 and that the catheter system comprises a drive unit 11 for manipulating the tip 62. The user of the catheter system uses the steering system 30 to move the catheter 5 and its tip 62 to a required position within the body 13. For this purpose the catheter system comprises a motor steering device 9 for steering the motor device 21 of the steering system 30. The user further uses the drive unit 11 to manipulate the tip 62 in order to execute a desired operation by the tip on the body 13. The body can be among others a human body, e.g. a patient, or an animal body.

Figure 4:
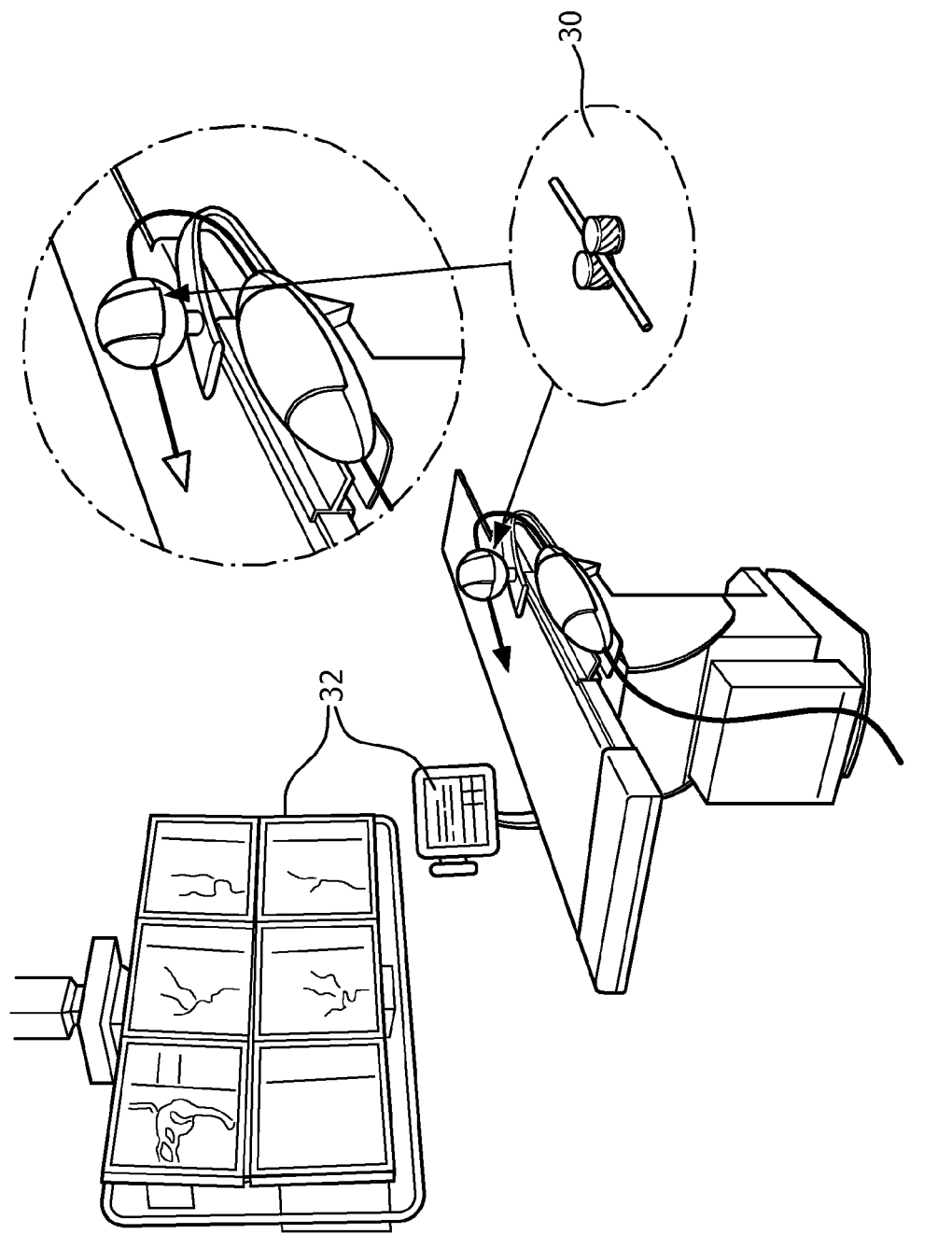
FIG. 4 schematically shows a second exemplary embodiment of the catheter system according to the invention wherein a display, showing the position of a tip of the catheter, is shown.

FIG. 4 schematically shows an exemplary embodiment of the catheter system according to the invention wherein a display 32 for showing the position of the tip of the catheter is shown. The user of the catheter system needs to know the position of the tip 62 in order to bring the tip in the desired position in the body 13 by the steering system 30. Once the tip 62 is positioned in the said desired position, the user needs to know orientation of the tip 62 in order to execute a desired operation on the body 13 by manipulating the tip using the drive unit 11. For this purpose the catheter system comprises a tracking means for determining a position and\or an orientation of the tip 62 in the body 13 and the display 32 for displaying the position and\or the orientation of the tip 62 determined by the tracking means.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any possible combination of such features is part of the invention. Any reference signs in the claims should not be construed as limiting the scope.

List of Reference Numerals
1, 3 drive wheels
5 a tubular object\a catheter
7 rollers
9 a motor steering device
11 a drive unit
13 a patient
21 a motor device
30 a steering system
32 a display
40, 42 wheel rotation axes
44 a roller rotation axis
50, 52 wheel flanges
52 a second base of the wheel
54 a first end of the roller
56 a second end of the roller
58 an outer drive face
60 a drive wheels control device
62 a tip

The invention claimed is:

1. A steering system comprising two radially oppositely arranged drive wheels for steering a tubular object positioned between the drive wheels, which drive wheels each have a wheel rotation axis and each include a plurality of rollers distributed around the wheel rotation axis, which rollers are rotatably arranged, each roller having a roller rotation axis and an outer drive face concavely vaulted in a direction corresponding to its roller rotation axis, wherein the roller rotation axis is obliquely oriented in relation to the wheel rotation axis and wherein the rollers of each drive wheel form together a steering periphery for the tubular object.

2. The steering system as claimed in claim 1, wherein the roller rotation axis forms an angle between 10 and 80 degrees, preferably between 30 and 60 degrees with the wheel rotation axis.

3. The steering system as claimed in claim 1, wherein the roller rotation axis forms an angle of substantially 45 degrees with the wheel rotation axis.

4. The steering system as claimed in claim 1, wherein the drive wheels are moveable between a first position in which the driving wheels are close to each other for driving the tubular object and a second position in which the driving wheels are remote from each other for plugging in and\or out the tubular object.

5. The steering system as claimed in claim 1, wherein the steering system comprises a motor device for driving the drive wheels.

6. The steering system as claimed in claim 1, wherein each drive wheel includes two wheel flanges extending around the rotation axis, wherein the rollers are mounted between the two wheel flanges.

7. The steering system as claimed in claim 1, wherein the wheel rotation axes are substantially parallelly arranged.

8. The steering system as claimed in claim 4, wherein the steering system comprises a drive wheels control device for moving the drive wheels between the first position and the second position.

9. A catheter system comprising: a catheter, and the steering system as claimed in claim 1, wherein the catheter constitutes the tubular object.

10. The catheter system as claimed in claim 9, wherein the catheter comprises a tip and wherein the catheter system comprises a drive unit for manipulating the tip.

11. The catheter system as claimed in claim 9,
wherein the steering system comprises a motor device for driving the drive wheels; and
wherein the catheter system comprises a motor steering device for steering the motor device of the steering system.

12. The catheter system as claimed in claim 9, wherein the catheter system comprises a tracking means for determining a position and\or an orientation of the tip in a body and further comprises a display for displaying the position and\or the orientation of the tip determined by the tracking means.

13. The catheter system as claimed in claim 9, wherein the wheels of the steering system are constituted as a disposable unit.

* * * * *